United States Patent
Porto

(10) Patent No.: US 7,803,101 B2
(45) Date of Patent: Sep. 28, 2010

(54) RANDOM ACCESS MULTI-DISC CENTRIFUGE

(75) Inventor: Johannes Porto, Fairport, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 834 days.

(21) Appl. No.: 11/668,496

(22) Filed: Jan. 30, 2007

(65) Prior Publication Data

US 2008/0182742 A1    Jul. 31, 2008

(51) Int. Cl.
*B04B 5/10* (2006.01)
(52) U.S. Cl. ............... 494/11; 494/34; 494/37
(58) Field of Classification Search ........ 494/1, 494/7, 11, 37, 43, 84, 31, 34; 422/72; 436/45; 366/213–214
See application file for complete search history.

(56) References Cited

U.S. PATENT DOCUMENTS

| | | | | |
|---|---|---|---|---|
| 2,006,451 | A * | 7/1935 | Glidden | 366/213 |
| 3,902,660 | A * | 9/1975 | Barber | 494/11 |
| 4,228,950 | A | 10/1980 | Ito | |
| 4,874,358 | A * | 10/1989 | Brimhall et al. | 494/37 |
| 5,552,064 | A | 9/1996 | Chachowski et al. | |
| 5,650,068 | A | 7/1997 | Chachowski et al. | |
| 6,461,287 | B1 * | 10/2002 | Glater | 494/16 |
| 6,593,143 | B1 * | 7/2003 | Gordon | 436/45 |
| 6,605,223 | B2 | 8/2003 | Jorgensen et al. | |
| 7,195,737 | B2 * | 3/2007 | Itoh | 422/72 |
| 2004/0089737 | A1 * | 5/2004 | Itoh | 239/264 |
| 2008/0182742 | A1 * | 7/2008 | Porte | 494/7 |

FOREIGN PATENT DOCUMENTS

| | | | |
|---|---|---|---|
| JP | 02277022 A | * | 11/1990 |
| WO | WO 0197943 A1 | | 12/2001 |
| WO | WO 2005007296 A1 | | 1/2005 |

* cited by examiner

*Primary Examiner*—Charles E Cooley
(74) *Attorney, Agent, or Firm*—Todd J. Burns

(57) ABSTRACT

A centrifuge includes: a plurality of centrifuge discs each disc having an attachment for attaching a container containing a liquid to be centrifuged; a disc driver positioned to engage and rotate the discs; a disc engager/disengager for individually moving each of said discs into and out of contact with the disc driver; and a controller for controlling which discs are engaged or disengaged from the disc driver and the amount of time each disc is centrifuged. In another embodiment, the centrifuge includes a plurality of disc drivers positioned to engage and rotate the discs, wherein the rotation of discs are controlled by the plurality of disc drivers; and a controller for controlling which discs are rotated by the plurality of disc drivers and the amount of time the discs are centrifuged by individually controlling each disc driver.

13 Claims, 5 Drawing Sheets

RANDOM ACCESS MULTI-DISC CENTRIFUGE

BACKGROUND OF THE INVENTION

The present invention relates to a centrifuge and a method for centrifuging containers, in particular cards for blood typing such as gel or bead type cards. In particular the present invention relates to a random access centrifuge having independently accessible rotors and a method for independently centrifuging containers, particularly cards for blood typing.

Known blood typing (immunohematology) analyzers include analyzers such as the Vitros® Provue and Autovue by Ortho-Clinical Diagnostics, Inc. Currently there are two methods of immunohematology testing. They are manual and automated. The manual method requires the operator to manually load the cards into a centrifuge. The automated method (Provue and Autovue) places the cards into a centrifuge automatically following an incubation period. In both cases, the cards are loaded in batch mode. This requires the centrifuge to wait until all the cards are loaded before beginning the separation process, and it prevents the operator or the analyzer from processing more cards until the centrifuge completes its cycle. The separation operation of the test is the longest at 10 minutes. This results in increased centrifugation time and hence an overall increase in the analysis cycle time.

For the foregoing reasons, there is a need for a centrifuge and method of centrifugation that reduces overall centrifugation time.

SUMMARY OF THE INVENTION

The present invention is directed to an apparatus and method that solves the foregoing problems of excessive centrifugation time and overall cycle time, by providing multiple centrifugation discs or rotors that can be selectively rotated by the centrifugation system.

One aspect of the invention is directed to a centrifuge which includes: a plurality of centrifuge discs each disc having an attachment for attaching a container containing a liquid to be centrifuged; a disc driver positioned to engage and rotate the discs; a disc engager/disengager for individually moving each of the discs into and out of contact with the disc driver; and a controller for controlling which discs engaged or disengaged from the disc driver and the amount of time each disc is centrifuged. In a preferred embodiment, the container is a card for blood typing.

Another aspect of the invention provides a centrifuge which includes: a plurality of centrifuge discs each disc having an attachment for attaching a container containing a liquid to be centrifuged; a plurality of disc drivers positioned to engage and rotate the discs, wherein the rotation of discs are controlled by the plurality of disc drivers; and a controller for controlling which discs are rotated by said plurality of disc drivers and the amount of time the discs are centrifuged by individually controlling each disc driver. In a preferred embodiment, the container is a card for blood typing such as a gel or bead type card.

Another aspect of the invention provides an immunohematology instrument which includes: a centrifuge which comprises a plurality of centrifuge discs each disc having an attachment for attaching a blood typing card containing blood to be centrifuged; a disc driver positioned to engage and rotate the discs; a disc engager/disengager for individually moving each of the discs into and out of contact with the disc driver; and a controller for controlling which discs are engaged or disengaged from the disc driver and the amount of time each disc is centrifuged; an incubator; a metering apparatus; an imaging apparatus; blood typing card storage; and reagent storage.

Yet another aspect of the invention provides a method for centrifuging a multiple containers independently comprising: providing a centrifuge as described above; attaching one or more containers to the centrifuge discs; engaging the centrifuge discs with the disc driver to commence centrifugation; disengaging one or more of the centrifuge discs based on a signal from the controller.

Further objects, features and advantages of the present invention will be apparent to those skilled in the art from detailed consideration of the preferred embodiments that follow.

DETAILED DESCRIPTION OF PREFERRED EMBODIMENTS

The present invention is directed to a solution of eliminating the wait time required for a container, such as a blood typing card, to centrifuge by providing a random access centrifuge in which a plurality of multiple centrifuge discs are provided. When a container is placed onto the disc, such as through a load slot, the disc with the container can be centrifuged without waiting for other containers to be placed onto other rotors.

Description will be made to the non-limiting embodiments shown in the figures. As shown in the FIG. 1 embodiment, the large diameter discs are independent centrifuges (20A-20F). While the FIG. 1 embodiment shows six centrifuge discs, the present invention is not so limited, the number of discs can range from two up to any number desired. The centrifuge discs rotate about spindle (21). The centrifuge disc (20F) is shown in the load/unload position.

Figure 2:
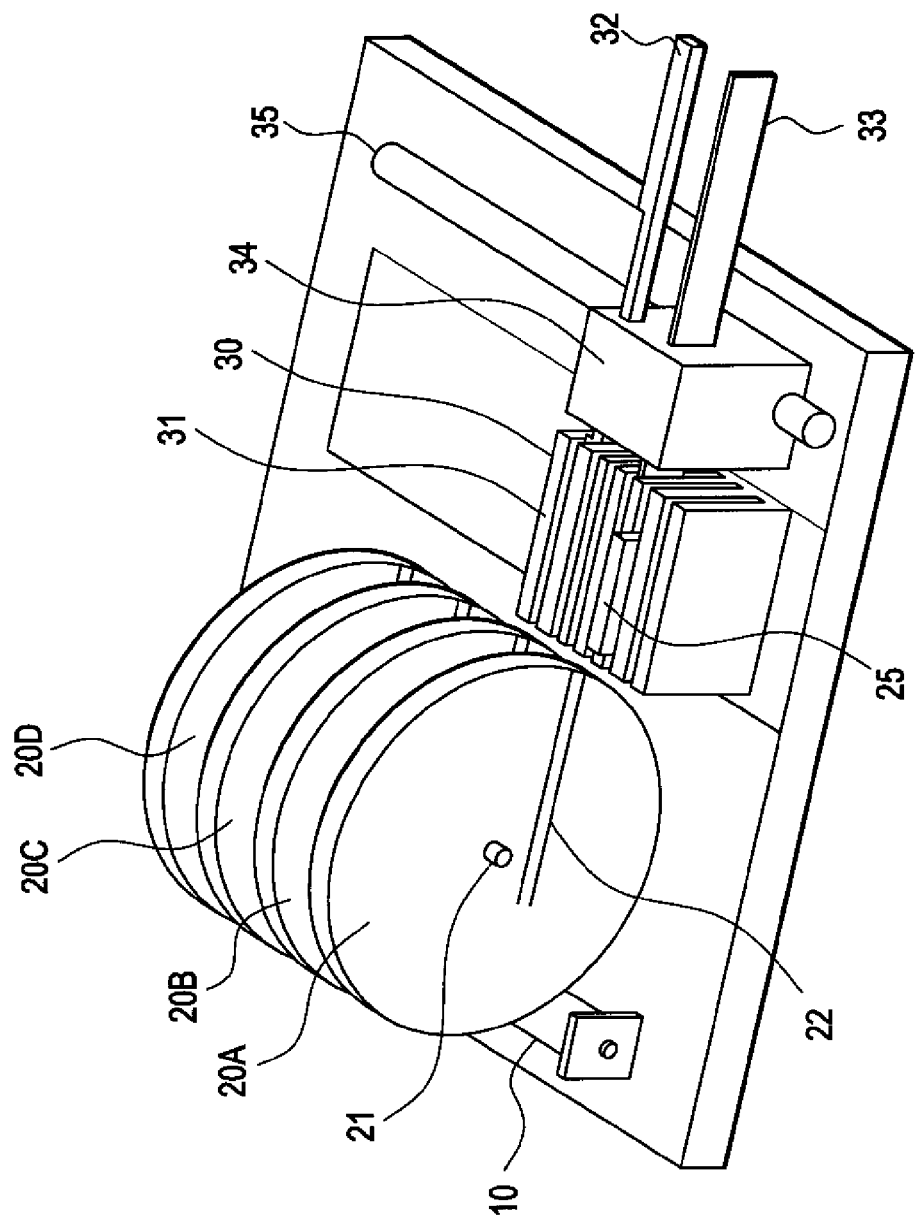
FIG. 2 is a perspective schematic view of a centrifuge having separately controllable centrifuge discs according to a second embodiment of the invention.

In a preferred embodiment where the container is a gel card, incubator (30) holds gel cards in individual slots (31). The incubator (30) shuttles from side to side, lining up the gel card with the next available centrifuge or lining up an empty slot (31) to unload the completed gel card (25). To retain the container, an attachment (22, FIG. 2) is provided on the centrifuge disc. In a preferred embodiment, the attachment is a slot the gel card can slide into. The gel cards can be removed by picker blade (32) as shown in FIG. 2. The cards can be inserted into the centrifuge disc from the incubator by pusher blade (33). Both the picker and pusher blade are supported by alignment block (34), which can move along with incubator (30) along guide rail (35). After the container is loaded, the disc moves into contact with the driver (described below), which brings the centrifuge up to speed. The discs can be loaded, spun and unloaded separately from other discs.

Figure 1:
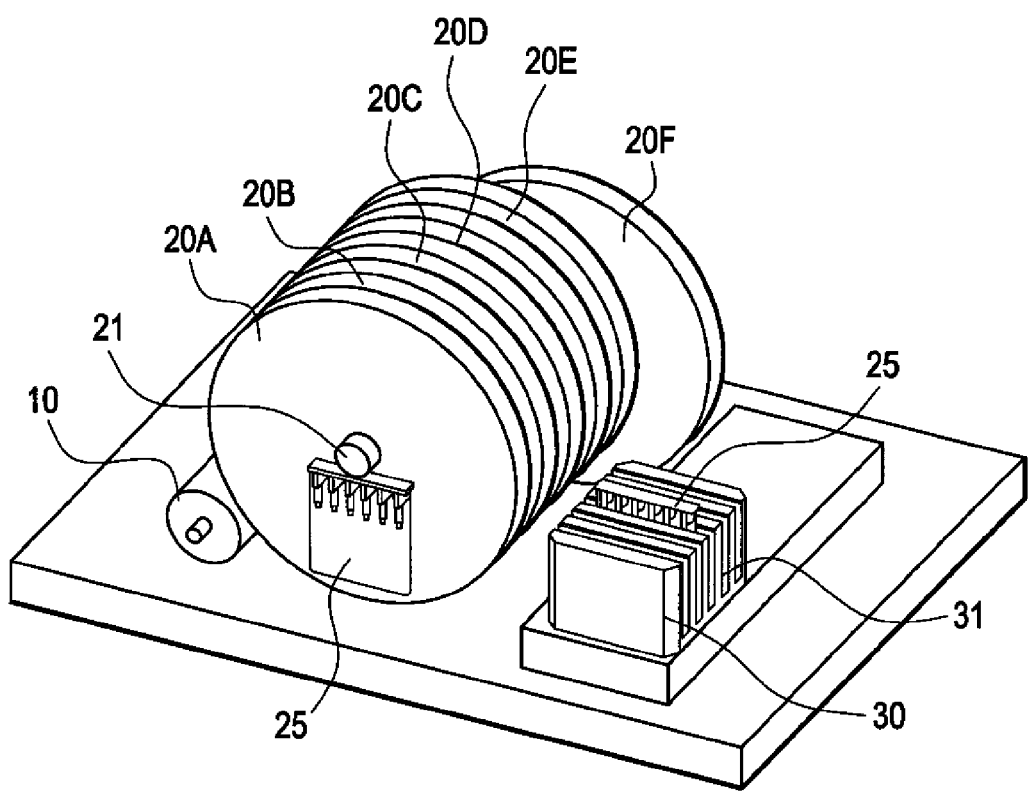
FIG. 1 is a perspective schematic view of a centrifuge having separately controllable centrifuge discs according to a first embodiment of the invention.
Figure 3:
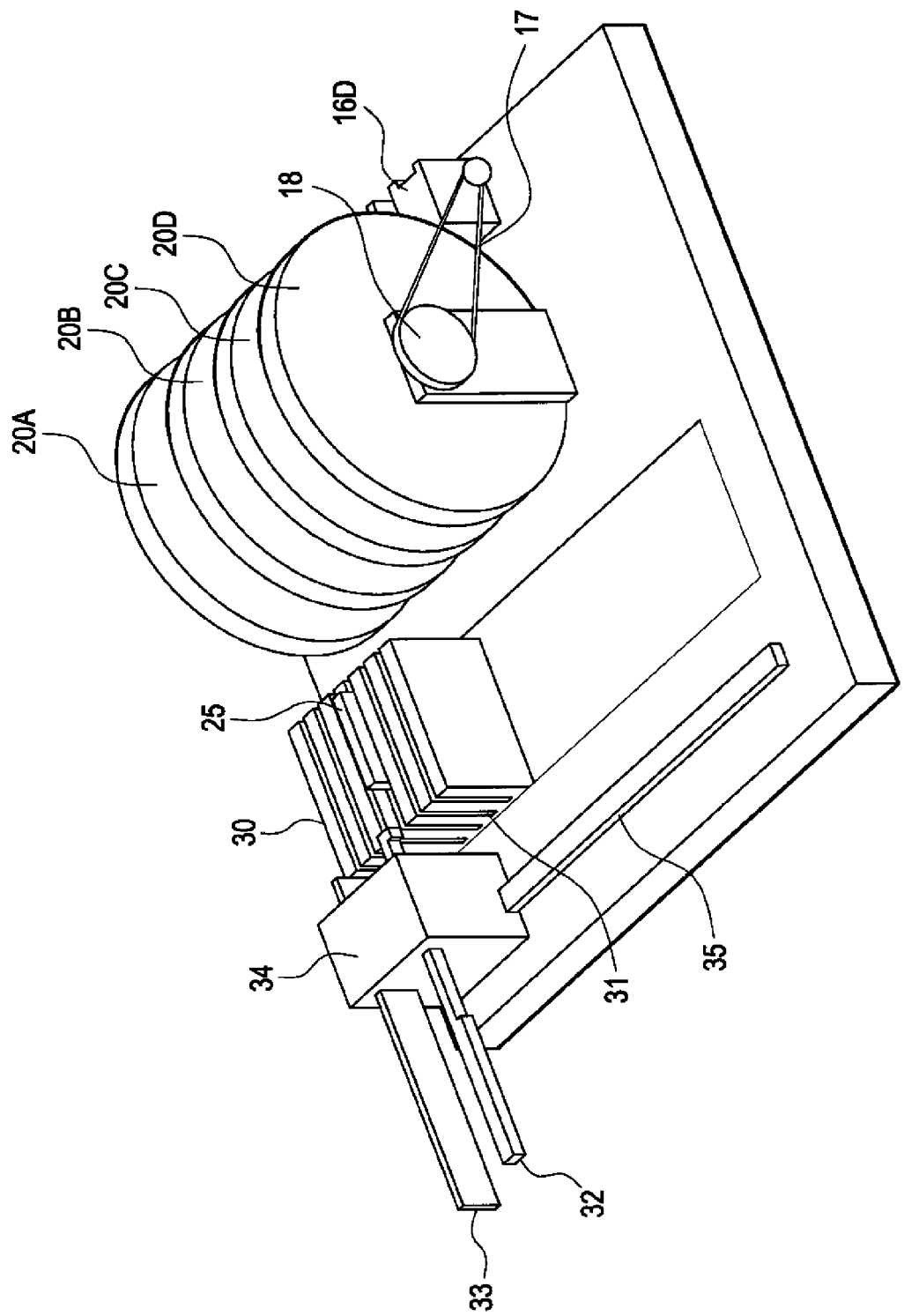
FIG. 3 is a perspective schematic view of a centrifuge having separately controllable centrifuge discs according to a third embodiment of the invention.
Figure 4:
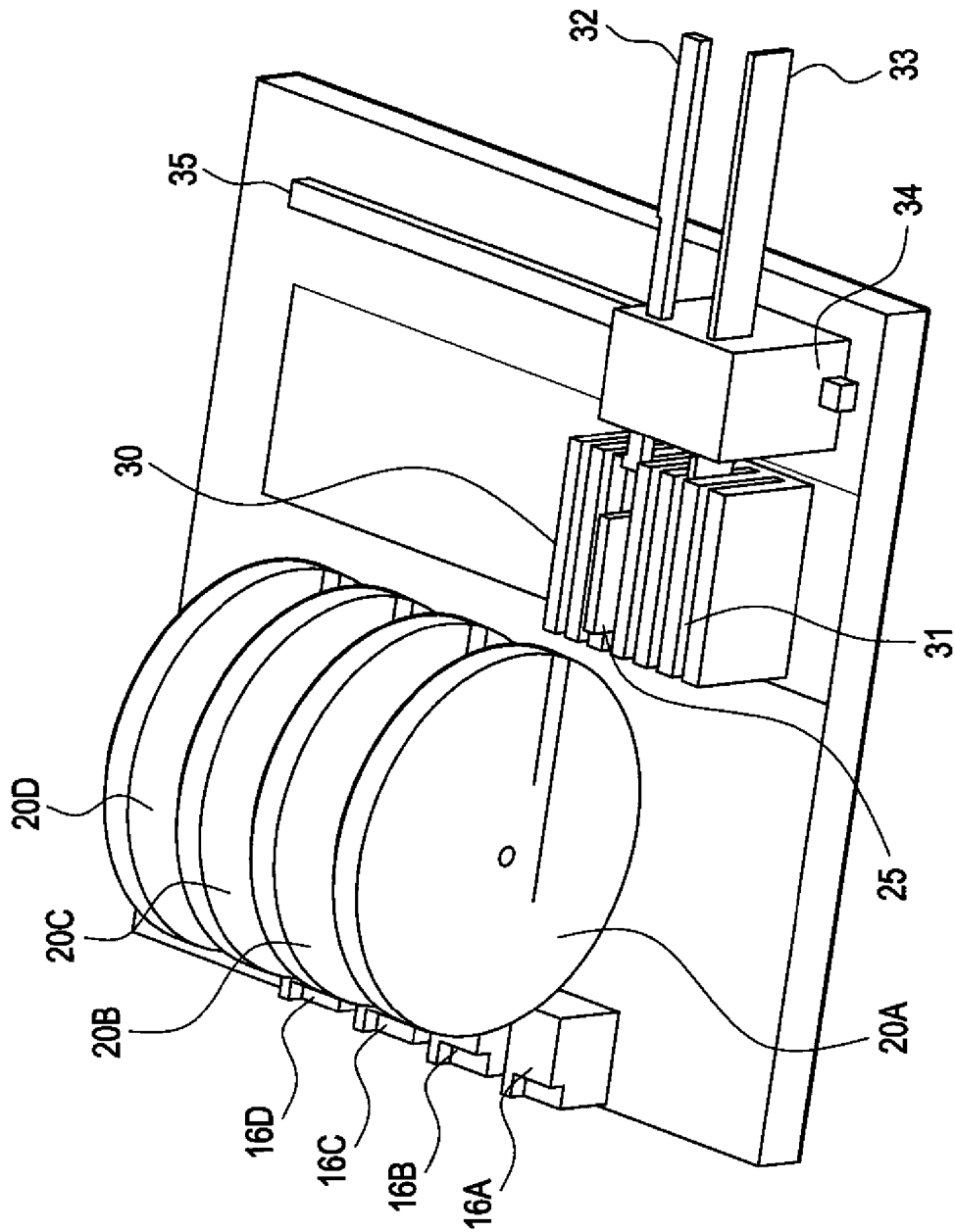
FIG. 4 is a perspective schematic view of a centrifuge having separately controllable centrifuge discs according to the third embodiment of the invention.

A driver is provided for rotating the centrifuge discs. In a preferred embodiment, a motor (15, FIG. 5) which can be a constant or variable speed motor, depending on the sample being centrifuged, drives the small roller (10) as shown in FIG. 1. In other embodiments, the centrifuge discs can be driven by multiple disc drivers. This can be accomplished through multiple motors (16A-16D, FIG. 4) driving each segment independently, such as through belt (17) connected to motor and pulley (18, FIG. 3). Alternatively, in some embodiments, the small roller (10) can be divided into segments to rotate at different speeds. For example, each disc segment can be rotationally connected through transmissions between each segment, which can step up or step down the rotation vis-á-vis the other disc segments. This is useful if different samples are being centrifuged that require different speeds. If individual disc drivers are used, the speed and duration of rotation can be controlled by controlling the individual disc drivers. The speed of the driver and length of rotation can be controlled by the control system described below.

Figure 5:
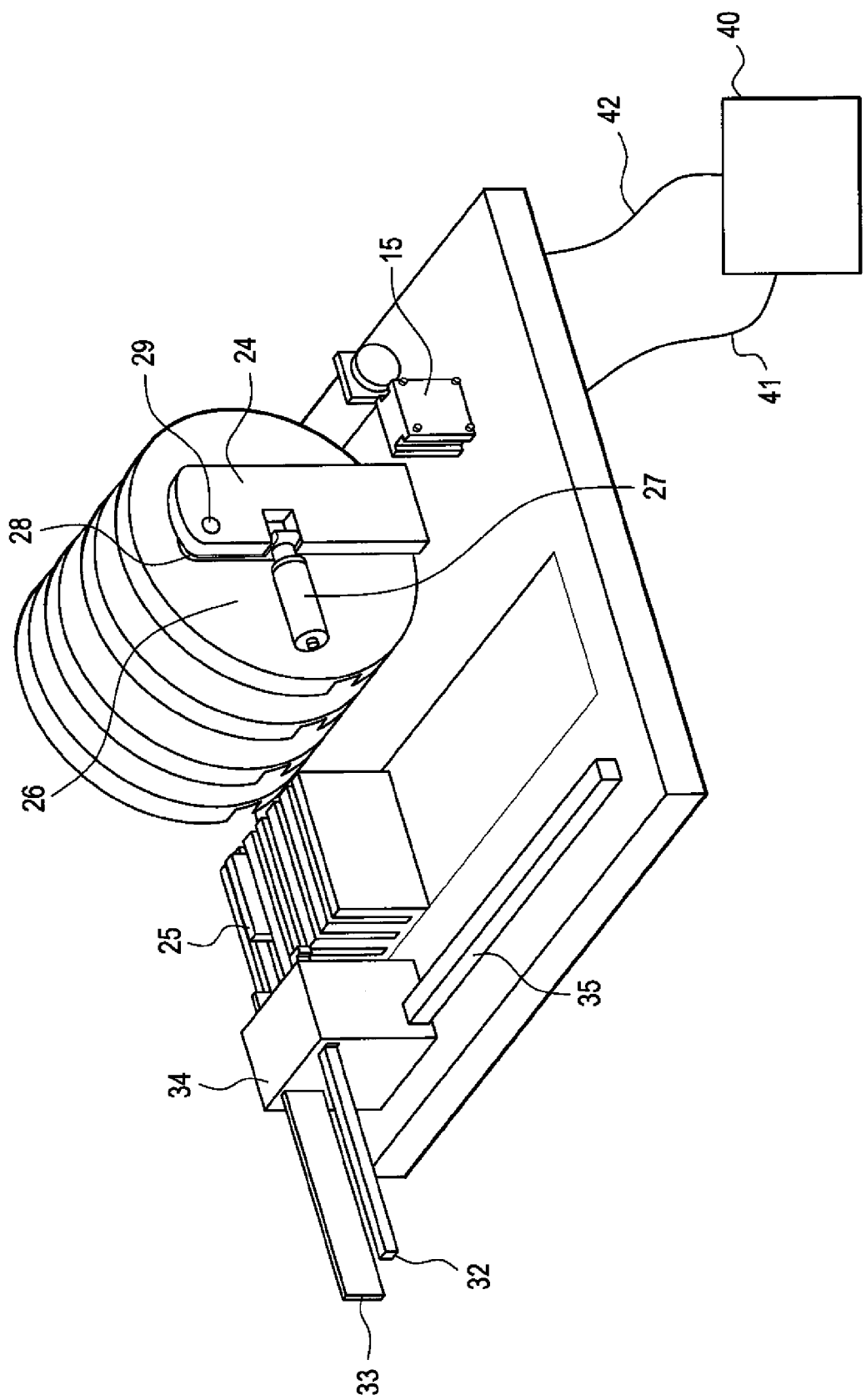
FIG. 5 is a perspective schematic view of a centrifuge having separately controllable centrifuge discs according to the second embodiment of the invention.

In those embodiments where at least two centrifuge discs are driven by the same disc driver, it will be necessary to engage and disengage the discs from the driver. To achieve this, a disc engager/disengager (26) is provided as shown in FIG. 5. Any suitable device for removing the disc from the driver can be used. In the preferred embodiment shown in FIG. 5, a pusher solenoid is (27) is attached to arm (28). The proximal end of arm (28) is in contact with solenoid (27) and supports spindle (21) through the axis of rotation of the disc. The distal end of arm (28) is pivotably connected to support (24). Upon actuation of the solenoid, the arm (28) pushes the disc out of contact with the disc drive by causing the arm (28) to rotate about pivot point (29). For each disc, a separate engager/disengager is preferably provided. Only one engager/disengager is shown for the sake of clarity.

In another embodiment, each disc has a pair of arms attached at the spindles at the proximal end of the arms and extend past the periphery of the disc. The distal end of the arms are connected to a device that, upon a signal from the control system, engage or disengage the disc from the disc driver. In a preferred embodiment, the device includes a servo motor having a pinion on its driveshaft. On the distal end of the arms is a rack that engages with the pinion of the servo motor. Up activation of the servo motor, the rack advances the centrifuge disc towards and away from the disc driver.

A control system, shown schematically as (40) in FIG. 5, is also provided. Control systems having sensors such as optical sensors, are well known in the art and are not discussed in depth. The control systems can be used to control the speed of rotation of the centrifuge discs, engaging or disengaging the centrifuge discs, controlling the operation of the picker and pusher blade and movement of the incubator. The control system shown in FIG. 5, also schematically illustrate output 41 from the controller and input 42 to the controller.

The present invention also provides a method for independently centrifuging multiple containers. The containers are attached to the centrifuge discs. One advantage of the present invention is it is not necessary to wait to attach all containers to the centrifuges before centrifuging. In the present invention, once a container is attached to the centrifuge disc, the centrifugation can start while the other containers with samples are being prepared. The present method is also useful for concurrently centrifuging different samples that require different centrifugation times. The control system can determine the amount of time that each sample has been centrifuged and stop or disengage the particular centrifuge disc at the appropriate time for that particular sample.

As noted above, the present invention is particularly useful with cards such as gel or bead type for immunohematology instruments, such as the AutoVue® and ProVue® both sold by Ortho-Clinical Diagnostics, Inc. and used for blood typing. The cards are described in U.S. Pat. Nos. 5,650,068 and 5,552,064, which are incorporated herein by reference. In addition to the centrifuge, the immunohematology instruments include an incubator, metering apparatus, imaging apparatus, gel card storage and reagent storage, all of which are well known in the art.

The method for centrifuging multiple containers independently, particularly gel cards, can be implemented by a computer program, having computer readable program code, interfacing with the computer controller of the analyzer as is known in the art.

It will be apparent to those skilled in the art that various modifications and variations can be made to the methods and apparatus of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

I claim:

1. A centrifuge comprising:
   a plurality of centrifuge discs each disc having an attachment for attaching a container containing a liquid to be centrifuged;
   a disc driver positioned to engage and rotate said discs;
   a disc engager/disengager for individually moving each of said discs into and out of contact with the disc driver; and
   a
   a controller for controlling which discs are engaged or disengaged from said disc driver and the amount of time each disc is centrifuged.

2. A centrifuge as claimed in claim 1, wherein each centrifuge disc further comprises a spindle for supporting disc rotation thereon.

3. A centrifuge as claimed in claim 2, further comprising a pair of arms having a proximal end rotatably attached to the spindle and extending beyond the periphery of the disc, wherein the at least one of the distal ends of pair of arms are attached to the disc engager/disengager.

4. A centrifuge as claimed in claim 3, wherein the disc engager/disengager comprise a servo motor having a pinion in contact with a rack on at least on of the distal end of the arms.

5. A centrifuge as claimed in claim 2, wherein the engager/disengager comprises a pivotable arm, a support and a solenoid, wherein the distal end of the arm is in movable contact with the solenoid and supports the spindle, and wherein the proximal end of the arm is pivotably attached to the support to form a pivot point, whereby upon activation of the solenoid, the arm rotatably moves around the pivot point disengaging the disc from the disc drive.

6. A centrifuge as claimed in claim 1, wherein the disc engager/disengager are controlled by a controller.

7. A centrifuge as claimed in claim 1, wherein the container is a card for blood typing.

8. A combination card for blood typing and the centrifuge as claimed in claim 1.

9. A method for centrifuging multiple containers comprising:
   providing the centrifuge as claimed in claim 1;

attaching one or more containers to one or more centrifuge discs;

engaging the centrifuge discs with the disc driver to commence centrifugation;

disengaging one or more of the centrifuge discs based on a signal from the controller.

10. A method as claimed in claim 9, wherein the signal from the controller is based on the total centrifuge time for each container or the extent of centrifugation as monitored by a sensor.

11. A method as claimed in claim 10, wherein the sensor is an optical sensor.

12. A method as claimed in claim 9, wherein the containers are cards for blood typing.

13. An immunohematology instrument comprising: a centrifuge which comprises a plurality of centrifuge discs each disc having an attachment for attaching a gel card containing blood to be centrifuged;

a disc driver positioned to engage and rotate said discs;

a disc engager/disengager for individually moving each of said discs into and out of contact with the disc driver; and a a controller for controlling which discs are engaged or disengaged from said disc driver and the amount of time each disc is centrifuged;

an incubator;

a metering apparatus;

an imaging apparatus;

gel card storage; and reagent storage.

* * * * *